(12) United States Patent
Schmidt

(10) Patent No.: US 8,763,610 B2
(45) Date of Patent: Jul. 1, 2014

(54) RETENTION OF NOBLE GASES IN THE EXHALED AIR OF VENTILATED PATIENTS BY MEMBRANE SEPARATION

(76) Inventor: Klaus Schmidt, Gunzburg (DE)

( * ) Notice: Subject to any disclaimer, the term of this patent is extended or adjusted under 35 U.S.C. 154(b) by 935 days.

(21) Appl. No.: 12/309,570

(22) PCT Filed: Jul. 26, 2007

(86) PCT No.: PCT/EP2007/057720
§ 371 (c)(1),
(2), (4) Date: Oct. 1, 2009

(87) PCT Pub. No.: WO2008/012350
PCT Pub. Date: Jan. 31, 2008

(65) Prior Publication Data
US 2010/0031961 A1    Feb. 11, 2010

(30) Foreign Application Priority Data

Jul. 26, 2006   (DE) ......................... 10 2006 034 601

(51) Int. Cl.
*A61M 11/00*   (2006.01)

(52) U.S. Cl.
USPC ................. 128/205.27; 128/205.12; 128/910

(58) Field of Classification Search
USPC ........ 128/205.12, 205.27, 910; 95/47, 51, 54; 96/4
See application file for complete search history.

(56) References Cited

U.S. PATENT DOCUMENTS

| | | | | |
|---|---|---|---|---|
| 4,685,940 A * | 8/1987 | Soffer et al. | ......................... | 96/8 |
| 5,520,169 A * | 5/1996 | Georgieff et al. | ......... | 128/204.16 |
| 6,134,914 A * | 10/2000 | Eschwey et al. | ................ | 62/637 |
| 6,168,649 B1 * | 1/2001 | Jensvold et al. | ................... | 95/47 |
| 7,442,236 B2 * | 10/2008 | Taveira et al. | ................... | 96/111 |
| 2006/0130649 A1 * | 6/2006 | Jain et al. | ........................... | 95/82 |
| 2007/0017516 A1 * | 1/2007 | Schmidt | .................... | 128/204.23 |
| 2008/0029091 A1 * | 2/2008 | Mullner | ................... | 128/203.12 |
| 2009/0126733 A1 * | 5/2009 | Kulkarni et al. | ......... | 128/203.16 |

FOREIGN PATENT DOCUMENTS

| | | | | |
|---|---|---|---|---|
| DE | 4411533 C1 | 4/1994 | ............ | A61M 16/01 |
| DE | 19635002 A1 | 8/1996 | ............ | B01D 53/00 |
| DE | 19645223 | 1/1998 | ................ | F25J 3/06 |
| DE | 19646791 A1 | 5/1998 | ............. | C01B 23/00 |
| DE | 10300141 A1 | 1/2003 | ............ | B01D 53/22 |
| DE | 69717215 T2 | 7/2003 | ............ | B01D 53/00 |
| DE | 102005032977 B3 | 7/2005 | ............ | A61M 16/12 |
| EP | 428052 A2 | 11/1990 | ............ | B01D 69/10 |
| EP | 0621071 A1 | 4/1994 | ............ | B01D 53/22 |
| EP | 0806215 A2 | 11/1997 | ............ | A61M 16/01 |
| EP | 1086973 A2 | 3/2001 | ............ | C08G 73/10 |
| GB | 2207666 A | 8/1987 | ............ | C01B 31/02 |

(Continued)

*Primary Examiner* — Steven Douglas
(74) *Attorney, Agent, or Firm* — Head, Johnson & Kachigian, P.C.

(57) ABSTRACT

The processing of gas mixtures, in particular, of respiration gases for ventilated patients. The processing according to the invention relates, in particular, to the use of selective gas separation membranes for the retention of noble gases in the exhaled air of ventilated patients. The gas separation membrane is an active separator which is integrated in a ventilator. The separation membrane separates the noble gases from the remainder of the residual of the exhaled air by selectively retaining the noble gases. Thus, it is possible to provide a ventilator which enables the application of noble gases, in particular xenon, as an anesthetic preferably with low loss and as simple as possible.

5 Claims, 1 Drawing Sheet

(56) References Cited

FOREIGN PATENT DOCUMENTS

| WO | 98/18718 | 5/1998 | ............ C01B 23/00 |
| WO | 01/24858 A | 4/2001 | ............ A61M 16/00 |
| WO | WO 03092778 A1 * | 11/2003 | |
| WO | WO 2005092417 A1 * | 10/2005 | |
| WO | 2007/006377 A1 | 1/2007 | ............ A61M 16/00 |

* cited by examiner

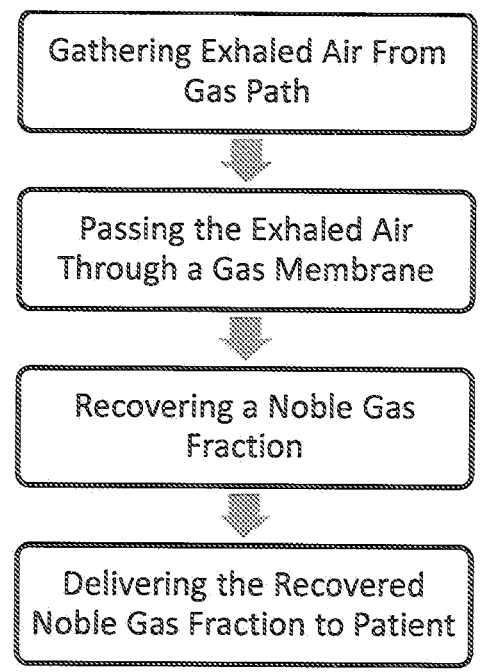

RETENTION OF NOBLE GASES IN THE EXHALED AIR OF VENTILATED PATIENTS BY MEMBRANE SEPARATION

CROSS REFERENCE TO RELATED APPLICATIONS

This application is the US National Phase of published PCT Application No. PCT/EP2007/05772 filed 26 Jul. 2007, which is incorporated herein by reference, which claims priority to German Patent Application No. 10 2006 034 601.7 filed 26 Jul. 2006.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to the treatment of gas mixtures, in particular the retention of noble gases in the exhaled air of ventilated patients. Especially, the present invention relates to the use of a selective gas separation membrane for retaining noble gases in the respiration gas of ventilated patients.

2. Description of the Invention

Among noble gases only xenon shows an anaesthetic effect under conditions of standard atmospheric pressure. This effect was demonstrated in 1941 by the Russian scientist Nikolay Vasilievich Lazarev.

The narcotic effect of xenon is 1.5 times stronger than that of nitrous oxide. Due to its extreme low blood solubility xenon will be exhaled more quickly than all other anaesthetics hitherto known. Additionally, xenon is environmentally friendly since it is neither harmful to the ozone layer nor is it a green-house gas. Xenon is inflammable and harmless to pregnant women. Apart from its anaesthetic property xenon is beneficial for the protection of the brain function of the patient. Xenon is particularly suitable for patients suffering from cardiovascular problems because during the anaesthesia with xenon the circulatory conditions of the patient remain extremely stable.

Due to its properties xenon shows advantages for specific indications compared to other anaesthetics. The material costs admittedly will be higher. The total costs for the treatment, however, will be markedly lower due to the advantageous activity profile, the minor side effects and the protective properties for organs while using xenon.

For the application in medicine the production of xenon will markedly rise in the future. But due to its chemical properties and its low availability and the costs associated with its production xenon is no alternative for nitrous oxide or established anaesthetics but is to complement them.

One possibility of cost-cutting will be to recycle and reuse the used xenon.

There are some cryogenic processes in the prior art.

DE 44 11 533 C1 describes an anesthesia apparatus having a recovery installation for xenon. In the recovery installation the pre-purified exhaled air is compressed and led into a pressure vessel which is included in a cooling device.

The pressure vessel is cooled by means of the cooling device so that the recovered xenon will be liquefied. The xenon from the exhaled air will be collected in the pressure vessel in a liquid state. From there, the xenon will be led back to the patient.

WO 98/18718 describes an apparatus and a process for purifying and recovering xenon in the anesthetic system, whereas xenon is collected in the liquid state in a cryogenic vessel after its purification and lead back to the patient.

DE 196 35 002 A1 describes a process for the online-recovery of xenon from narcotic gas, whereas the exhaled air is contacted with a cooling surface, the temperature of which is below the melting point of the component to be recovered. Hereby xenon will be separated by freezing and the impurities will be withdrawn in vacuo over the top gas.

WO 01/24858 A describes a system and a process with which gases, in particular humid gases such as expiration gases or exhaust gas from anesthetic instruments can be collected for recycling. The gas will be converted into a compressed form such as cold-worked or compressed gas in the gas compression vessel.

The mentioned systems are part of an anaesthetic system and are intended to directly recirculate the xenon to the patient during anaesthesia. Said systems and processes are accompanied by several problems regarding the instruments and the costs.

Hence, recently alternatives were searched for which allow a more simple and thus less expensive recycling of the xenon.

In this connection gas separation by an appropriate semi-permeable membrane, a so-called selective gas separation membrane plays an important role.

The separation of liquid, gaseous and vaporous mixtures of fluids by membranes is known in various processes. At least one of the components of the applied fluids is retained by the membrane and discharged in the form of a so-called retentate. At least another component of the fluid mixture will be able to permeate the membrane, which then will be discharged as permeate on the other side of the membrane.

Recently, however, techniques have been developed with which it was possible to produce sufficiently thin and therefore sufficiently permeable films for gas separation which are free of voids and mechanically stable. These types of membranes are based on very thin, nonporous and gas selective films on porous supporting layers.

From the prior art for example EP 428 052 gas separation membrane is known which is a semi-permeable composite membrane.

DE 697 17 215 T2 discloses a process for gas recovery, in particular of noble gases, from plasma display panel sealing furnaces by membrane separation.

DE 103 00 141 A1 describes an oxygen enrichment method from air by simultaneously reducing the carbon dioxide concentration in a closed or partially closed unit of space by means of a gas-purification membrane system. The used membranes have active layers of for example polysulfone, polyoctylmethylsiloxane, polyetherimide, silicon, ethylcellulose, polyphenylene oxid, polysulfone, polycarbonate as well as combinations thereof.

From EP 1 086 973 A2 gas separation means of polyimide, such as films, coatings and membranes are known, which are adapted for numerous fluid separation applications.

Use of gas separation membranes for the retention of noble gases in the exhaled air of ventilated patients has not been described so far.

BRIEF SUMMARY OF THE INVENTION

Accordingly, it is an object of the present invention to provide a simple process useful for the retention of noble gases, in particular xenon, within a gas mixture, for example the respiration gas for patients, with as low loss of xenon as possible.

A gas separation membrane is used for the recovery of noble gases contained in the exhaled air of ventilated patients.

The noble gas is selected from the group consisting of helium, neon, krypton, argon, xenon and mixtures thereof.

BRIEF DESCRIPTION OF THE DRAWING

FIG. 1 is a simple process in the retention of noble gases exemplary of the present invention.

In addition, the noble gas is xenon.

The gas separation membrane may be a microporous membrane.

The gas separation membrane may be a carbon molecular sieve membrane.

The gas separation membrane is part of a ventilator.

BRIEF DESCRIPTION OF THE INVENTION

This object is solved by use of a selective gas separation membrane for the recovery of noble gases contained in the exhaled air of ventilated patients in combination with the device and the process for the processing of gas mixtures described in the patent application DE 10 2005 032977.

The advantage of the present invention is that by using a selective gas separation membrane which is selective for noble gases for use in the plug-in for ventilators described in the patent application DE 10 2005 032977 it will be possible to use noble gases as sedatives, in particular xenon, for artificial respiration of patients at low costs. By the effect of using few instruments achieved thereby it will be possible to provide ventilators with which the expenditure of the noble gas can be reduced to a minimum by its recovery.

The gas separation membrane used for separating the noble gas fraction from the exhaled air should be characterized by a relatively low permeability for the desired noble gas or noble gas mixture. Additionally, the gas separation membrane should be characterized by a high degree of separation for the desired component to be separated from the gas mixture. In particular, the gas separation membrane should be selected so that the separation properties of the membrane will not be influenced by the humidity contained in the exhaled gas.

Gas separation membranes which are impermeable for the noble gases and noble gas mixtures to be separated for use in the present invention are known in the art. Examples for the use of such gas separation membranes can be found in several publications known to the skilled person, such as *Membrane Handbook*, Winston Ho und Kamalesch Sirkar, Springer 1992.

Preferred gas separation membranes are microporous membranes such as for example flexible and porous membranes based on oxidic and/or non-oxidic ceramics useful for separating and purifying fluids as described in DE 100 51 910 A1.

More preferred gas separation membranes for use according to the invention are microporous carbon membranes. Carbon membranes, their production and their use for the separation of various gases are known in the art, e.g. from U.S. Pat. No. 4,685,940, UK 2 207 666, EP 621 071 B1 and EP 0 621 071 B1.

According to the invention the gas separation membrane is used in a ventilator where the exhaled air from the patient is released into the environment (open circular flow of the main gas mixture). If a fraction useful for sedating a patient such as a noble gas such as xenon is added to the main components of the respiration gas it is desirable to recycle the unused part of the noble gas fraction and to re-supply the gas to the patient. This requires a selection element which separates the noble gas fraction from the other fractions of the exhaled air to enable recovery of the noble gas.

This requires a plug-in located in the gas path of the exhaled gas between the intubation tube and the open outlet for the exhaled gas comprising the above-mentioned selection element. Such a plug-in for use in a ventilator for patients is disclosed in the patent applications DE 10 2005 032977 and PCT/EP2006/05376.

The plug-in gas selection element according to the invention comprises the use of a selective semi-permeable gas separation membrane so that the noble gas fraction is separated from the rest of the expiration gas fraction and added to a fresh respiration gas mixture, whereby the noble gas portion is optionally newly adjusted and the thus treated respiration gas is re-supplied to the patient.

The noble gas fraction for example is separated by a membrane being selectively permeable for said noble gases from the expiration tube, whereas the rest of the expiration gas is released into the environment. Over a controllable supply regulator exhausted noble gas for the new respiration gas is added from a reservoir in a mixing chamber, to which a plug-in comprising the selection element is connected in series. The noble gas fraction separated from the expiration gas can be re-supplied to this reservoir. At this it is necessary to determine the amount of the noble gas fraction in the gas mixture which is to be re-supplied to the patient by means of a sensor. This may take place either in the mixing chamber or in the supply line, e.g. the intubation tube, to the mixing chamber.

The invention claimed is:

1. A process for recovery of a noble gas fraction from the expiration gas exhaled by a ventilated patient, which process comprises:
    gathering the expiration gas from an exhaled gas path fluidly connected to and downstream of an intubation tube, the intubation tube being fluidly connectable to the patient's mouth to receive the expiration gas therein;
    passing the expiration gas through a plug-in gas selection element located in the exhaled gas path, the plug-in gas selection element comprising a separation membrane impermeable to the noble gas fraction to separate the noble gas fraction from the rest of the expiration gas when the expiration gas contacts the separation membrane;
    releasing the rest of the expiration gas into the environment;
    retaining the noble gas fraction in the exhaled gas path;
    adding a fresh respiration gas mixture to the noble gas fraction to form a treated respiration gas; and
    delivering the treated respiration gas to the patient.

2. The process as set forth in claim 1 including the additional step of resupplying the noble gas fraction to the ventilator.

3. The process as set forth in claim 1 wherein the separation membrane is a microporous carbon molecular sieve membrane.

4. The process as set forth in claim 1 wherein the noble gas fraction is selected from the group consisting of at least one of: helium, krypton, argon and xenon.

5. The process as set forth in claim 4 wherein the noble gas fraction is xenon.

* * * * *